(12) United States Patent
Bagga et al.

(10) Patent No.: US 7,662,186 B2
(45) Date of Patent: Feb. 16, 2010

(54) ANTERIOR INTERBODY SPINAL IMPLANT

(75) Inventors: Charanpreet S. Bagga, Phoenixville, PA (US); Peter F. Ullrich, Jr., Neenah, WI (US); Michael E. Doran, Paoli, PA (US)

(73) Assignee: Titan Spine, LLC, Mequon, WI (US)

( * ) Notice: Subject to any disclaimer, the term of this patent is extended or adjusted under 35 U.S.C. 154(b) by 635 days.

(21) Appl. No.: 11/123,359

(22) Filed: May 6, 2005

(65) Prior Publication Data

US 2006/0265065 A1 Nov. 23, 2006

(51) Int. Cl.
*A61F 2/44* (2006.01)
(52) U.S. Cl. ............................... 623/17.16; 623/17.11
(58) Field of Classification Search .... 623/17.11–17.16
See application file for complete search history.

(56) References Cited

U.S. PATENT DOCUMENTS

| | | | | |
|---|---|---|---|---|
| 5,015,247 A * | 5/1991 | Michelson | ........... | 606/61 |
| 5,258,098 A | 11/1993 | Wagner et al. | ........... | 156/645 |
| 5,507,815 A | 4/1996 | Wagner et al. | ........... | 623/16 |
| 5,609,635 A * | 3/1997 | Michelson | ........... | 623/17.16 |
| 5,766,252 A | 6/1998 | Henry et al. | | |
| 5,922,029 A * | 7/1999 | Wagner et al. | ........... | 128/897 |
| 6,033,582 A * | 3/2000 | Lee et al. | ........... | 216/37 |
| 6,193,762 B1 | 2/2001 | Wagner et al. | ........... | 623/66 |
| 6,241,770 B1 | 6/2001 | Michelson | ........... | 623/17.11 |
| 6,241,771 B1 * | 6/2001 | Gresser et al. | ........... | 623/17.16 |
| 6,302,914 B1 * | 10/2001 | Michelson | ........... | 623/17.16 |
| 6,342,074 B1 * | 1/2002 | Simpson | ........... | 623/17.11 |
| 6,350,283 B1 | 2/2002 | Michelson | ........... | 623/17.11 |
| 6,432,140 B1 * | 8/2002 | Lin | ........... | 623/17.16 |
| 6,485,517 B1 | 11/2002 | Michelson | ........... | 623/17.11 |
| 6,491,723 B1 | 12/2002 | Beaty | ........... | 623/11.11 |
| 6,558,424 B2 | 5/2003 | Thalgott | ........... | 623/17.16 |
| 6,635,086 B2 * | 10/2003 | Lin | ........... | 623/17.11 |
| 6,730,127 B2 | 5/2004 | Michelson | ........... | 623/17.16 |
| 2001/0016777 A1 * | 8/2001 | Biscup | ........... | 623/17.16 |
| 2001/0047208 A1 * | 11/2001 | Michelson | ........... | 623/17.16 |
| 2002/0087212 A1 * | 7/2002 | James et al. | ........... | 623/17.11 |

(Continued)

FOREIGN PATENT DOCUMENTS

WO    WO 2004/041131    5/2004

*Primary Examiner*—Eduardo C Robert
*Assistant Examiner*—Julianna N Harvey
(74) *Attorney, Agent, or Firm*—Stradley Ronon Stevens & Young, LLP

(57) ABSTRACT

This present invention relates to interbody spinal implants and methods of using such implants. Certain embodiments of the present invention are particularly suitable for placement using an anterior surgical approach. Certain embodiments of the present invention include a body having a top surface, a bottom surface, opposing lateral sides, and opposing anterior and posterior portions. Interbody spinal implants, as now taught, further include roughened surface topography on at least a portion of its top surface and/or bottom surface. Preferred embodiments of the interbody spinal implant are substantially hollow and have a generally oval-shaped transverse cross-sectional area. Preferred embodiments of further include at least one aperture that extends the entire height of the implant body. This vertical aperture also defines a transverse rim having greater posterior thickness than anterior thickness. Certain embodiments also preferably include at least one aperture that extends the entire transverse length of the implant body.

13 Claims, 7 Drawing Sheets

U.S. PATENT DOCUMENTS

| | | | |
|---|---|---|---|
| 2002/0161443 A1* | 10/2002 | Michelson | 623/17.11 |
| 2003/0109928 A1* | 6/2003 | Pasquet et al. | 623/17.11 |
| 2003/0125739 A1* | 7/2003 | Bagga et al. | 606/61 |
| 2003/0153975 A1* | 8/2003 | Byrd et al. | 623/17.11 |
| 2003/0181981 A1* | 9/2003 | Lemaire | 623/17.11 |
| 2004/0117020 A1* | 6/2004 | Frey et al. | 623/17.11 |
| 2004/0127993 A1* | 7/2004 | Kast et al. | 623/17.16 |
| 2004/0230306 A1* | 11/2004 | Hoeck et al. | 623/17.11 |
| 2005/0027360 A1* | 2/2005 | Webb et al. | 623/17.11 |
| 2006/0100705 A1* | 5/2006 | Puno et al. | 623/17.11 |

\* cited by examiner

US 7,662,186 B2

ANTERIOR INTERBODY SPINAL IMPLANT

FIELD OF THE INVENTION

This invention relates to interbody spinal implants and methods of using such implants. The spinal implants are further particularly suitable for placement using an anterior surgical approach.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, develop deformities such as tears/cracks, or simply lose structural integrity, for example bulge or flatten. These impaired discs can affect the anatomical functions of the vertebrae, due to the resultant lack of proper biomechanical support, and are often associated with chronic back pain.

Several surgical techniques have been developed to address spinal defects, such as disc degeneration, deformity, or both. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or anterior approach. Anterior interbody fusion procedures generally have reduced operative times, reduced blood loss, and do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This is not, however, the preferable seating position for an implant system, since only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence into the softer cancellous bone of the vertebral body may arise from such improper seating.

In contrast, open ring-shaped cage implant systems are generally shaped to mimic the anatomical contour of the vertebral body. Traditional ring-shaped cages, however, are generally comprised of allograft bone material, harvested from the human femur, which restrict the usable size and shape of the resultant implant. For example, many of these femoral ring-shaped cages generally have a medial-lateral width of less than 25 mm. As such, these cages may not be of a sufficient size to contact the strong cortical bone, or apophyseal rim, of the vertebral endplate. These size-limited implant systems may also poorly accommodate related instrumentation such as drivers, reamers, etc. For example, these implants systems may lack sufficient structural integrity to withstand repeated impaction and may facture during implantation. Still further, other traditional non-allograft ring-shaped cage systems may be size-limited due to varied and complex supplemental implantation instrumentation which may obstruct the disc space while requiring greater exposure of the operating space. These supplemental implantation instrumentation systems also generally increase the instrument load upon the surgeon.

An implant system's corresponding surgical procedure should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants, as now taught, which better utilize the structurally supportive bone of the apophyseal rim.

SUMMARY OF THE INVENTION

The present invention is directed to interbody spinal implants and methods of using same. The interbody spinal implants are particularly suited for placement using an anterior surgical approach. Certain preferred embodiments of the present invention provide for an anatomically shaped spinal implant for improved seating in the disc space, particularly in the medial-lateral aspect of the disc space, and improved utilization of the vertebral apophyseal rim. Certain embodiments of the present invention further have a highly radiused posterior portion, and sides, which allow for ease of implantation. Thus, the posterior portion may have a generally blunt nosed profile. Preferred embodiments also allow for improved visualization of the disc space during surgical procedures while minimizing exposure of the operating space. Certain aspects of the invention may also reduce the need for additional instrumentation, such as chisels and/or reamers, to prepare the vertebral endplate, thus minimizing the instrument load upon the surgeon.

Preferred embodiments of the interbody implant are substantially hollow and have a generally oval-shaped transverse cross-sectional area. Substantially hollow, as used herein, means at least about 33% of the interior volume of the interbody spinal implant is vacant. Further preferred embodiments of the present invention include a body having a top surface, a bottom surface, opposing lateral sides, and opposing anterior and posterior portions. The implant includes at least one aperture that extends the entire height of said body. Thus, the aperture extends from the top surface to the bottom surface. The implant may further include at least one aperture that extends the entire transverse length of the implant body. Still further, the substantially hollow portion may be filled with cancellous autograft bone, allograft bone, demineralized bone matrix (DBM), porous synthetic bone graft substitute, bone morphogenic protein (BMP), or combinations thereof. The implant further includes roughened surface topography on at least a portion of its top and/or bottom surfaces. The anterior portion, or trailing edge, of the implant is preferably generally greater in height than the opposing posterior portion, or leading edge. Thus, the trailing edge is taller than the leading edge. The posterior portion and lateral sides may also be generally smooth and highly radiused, thus allowing for easier implantation into the disc space. Thus, the posterior portion may have a blunt nosed profile. The anterior portion, or trailing edge, of the implant may preferably be configured to engage a delivery device, a surgical driver or other surgical tools. The anterior portion may also be substantially flat.

DETAILED DESCRIPTION OF ILLUSTRATIVE EMBODIMENTS

Certain embodiments of the present invention may be especially suited for placement between adjacent human vertebral bodies. The implants of the present invention may be used in procedures such as cervical fusion and Anterior Lumbar Interbody Fusion (ALIF). Certain preferable embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain presently preferred aspects of the present invention, allow for improved visualization of implant seating and fusion assessment. Interbody spinal implants, as now taught, may also facilitate osteointegration with the surrounding living bone.

Anterior interbody spinal implants in accordance with certain aspects of the present invention can be preferably made of a durable material such as stainless steel, stainless steel alloy, titanium, or titanium alloy, but can also be made of other durable materials such as, but not limited to, polymeric, ceramic or composite materials. For example, certain embodiments of the present invention may be comprised of a biocompatible, polymeric matrix reinforced with bioactive fillers and/or fibers. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals and/or metal alloys. Titanium and its alloys are generally preferred for certain embodiments of the present invention due to their acceptable, and desirable, strength and biocompatibility. In this manner, certain preferred embodiments of the present interbody spinal implant may have improved structural integrity and may better resist fracture during implantation by impaction. Interbody spinal implants, as now taught, may therefore be used as a distractor during implantation.

Figure 1:
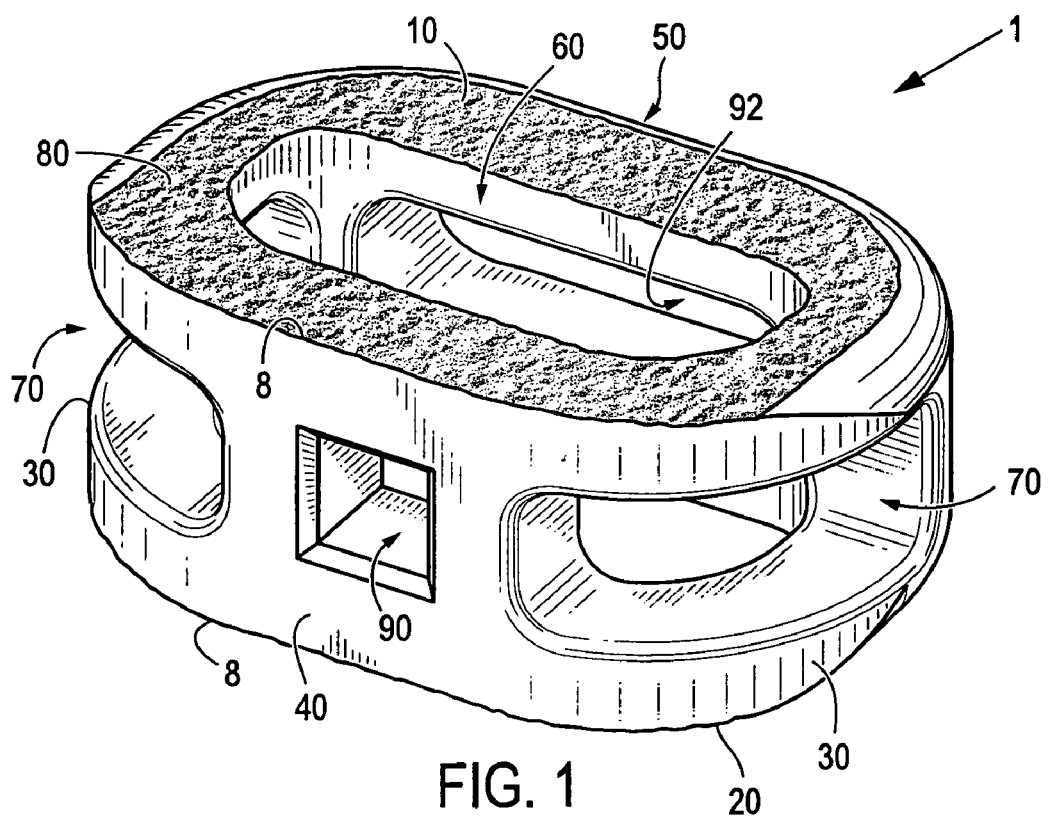
FIG. 1 shows a perspective view of a preferred embodiment of the interbody spinal implant (01) having a generally oval shape and roughened surface topography (80) of top surface (10).
Figure 2:
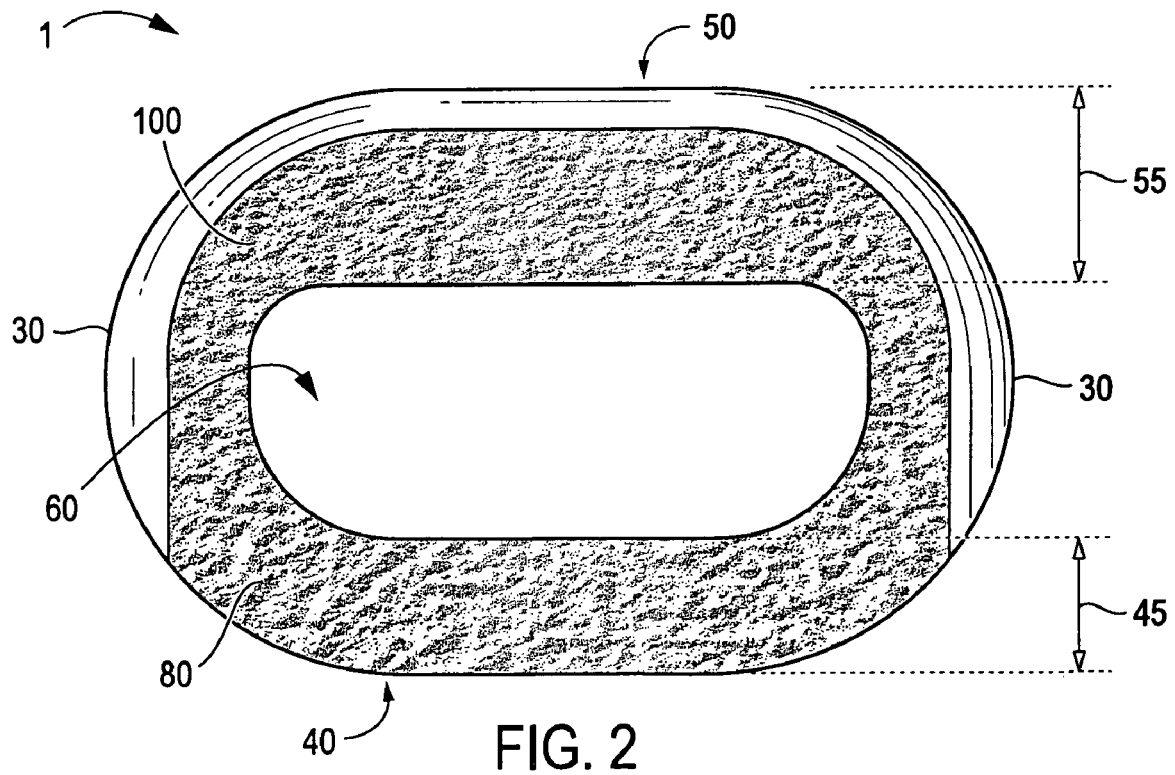
FIG. 2 depicts a top view of an embodiment of the interbody spinal implant (01).
Figure 3:
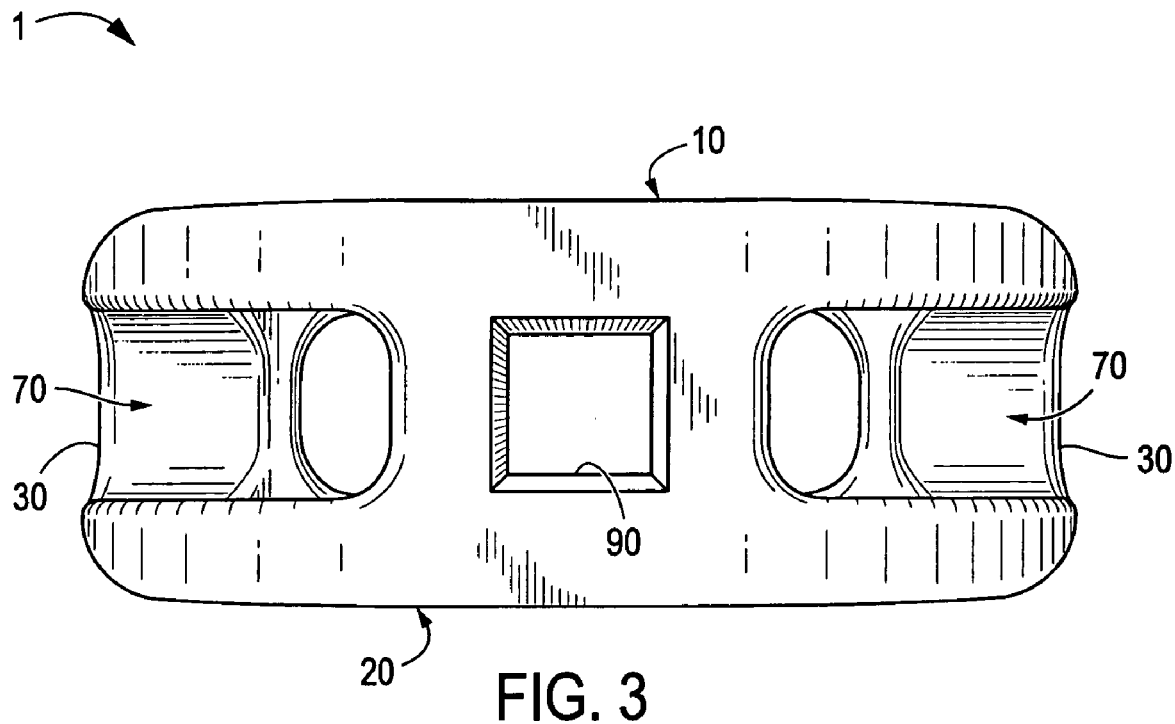
FIG. 3 depicts an anterior view of the same embodiment of interbody spinal implant (01).
Figure 4:
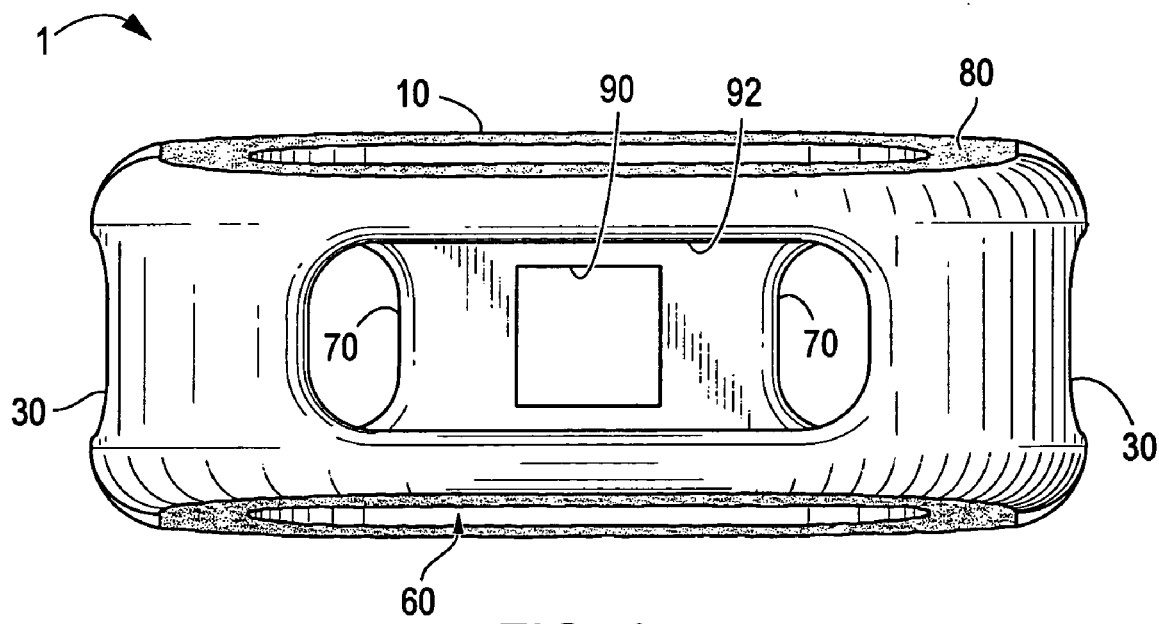
FIG. 4 depicts a posterior view of the same embodiment of interbody spinal implant (01).
Figure 5A:
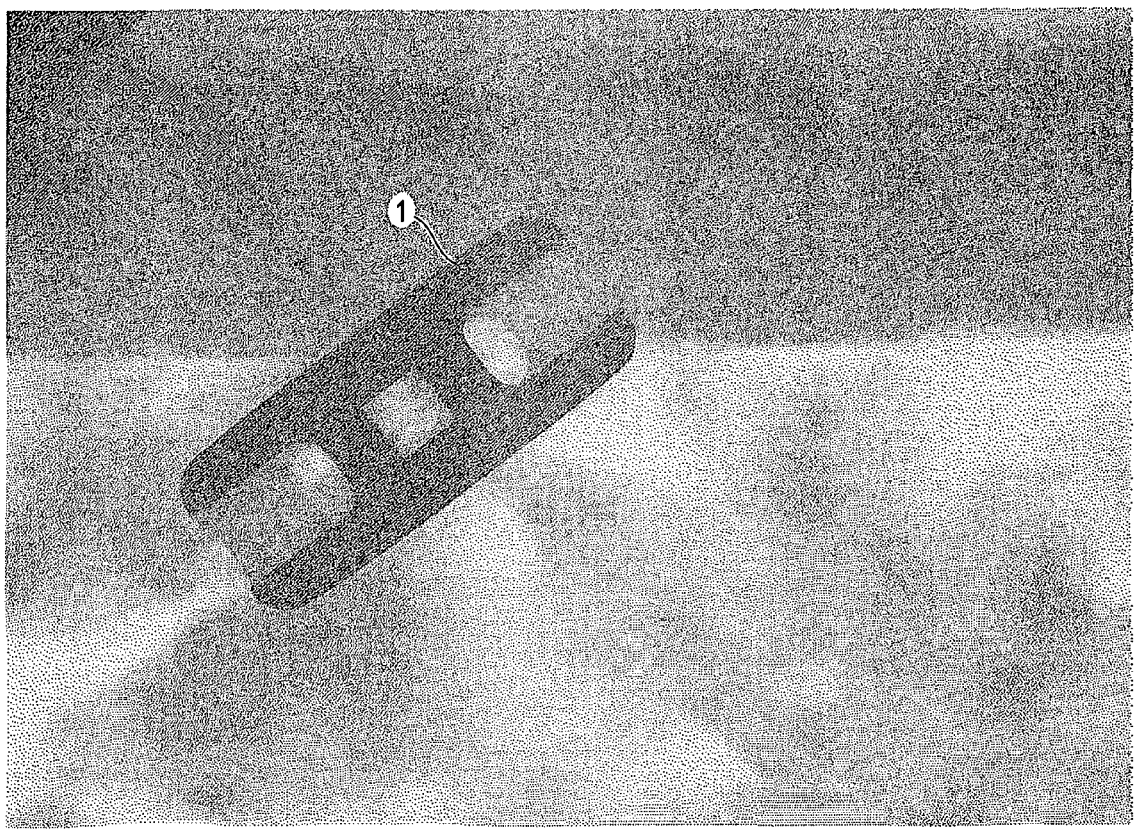
FIGS. 5A-5C depict various post-operative radiographs showing visualization of an embodiment of the interbody spinal implant.
Figure 5B:
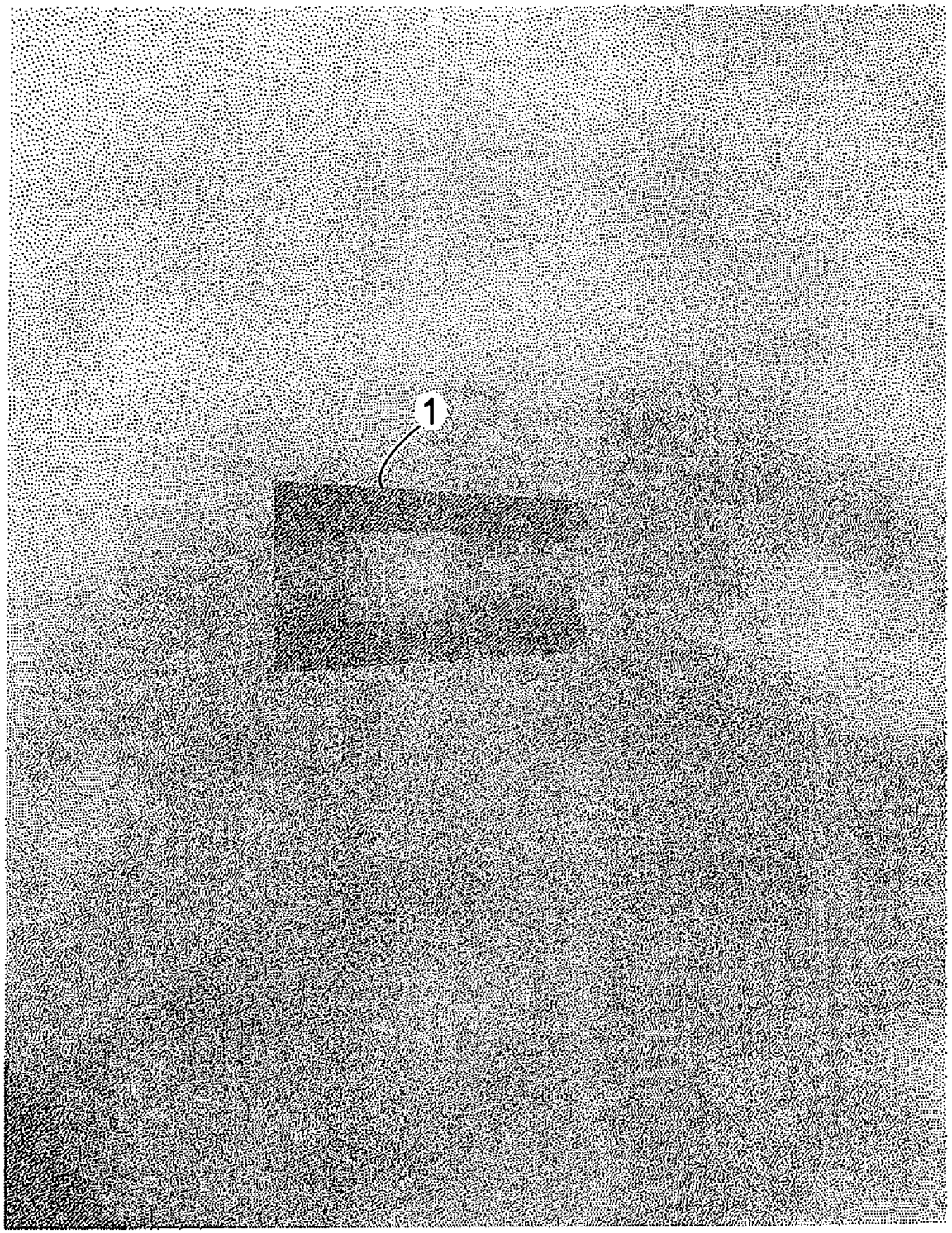
Figure 5C:
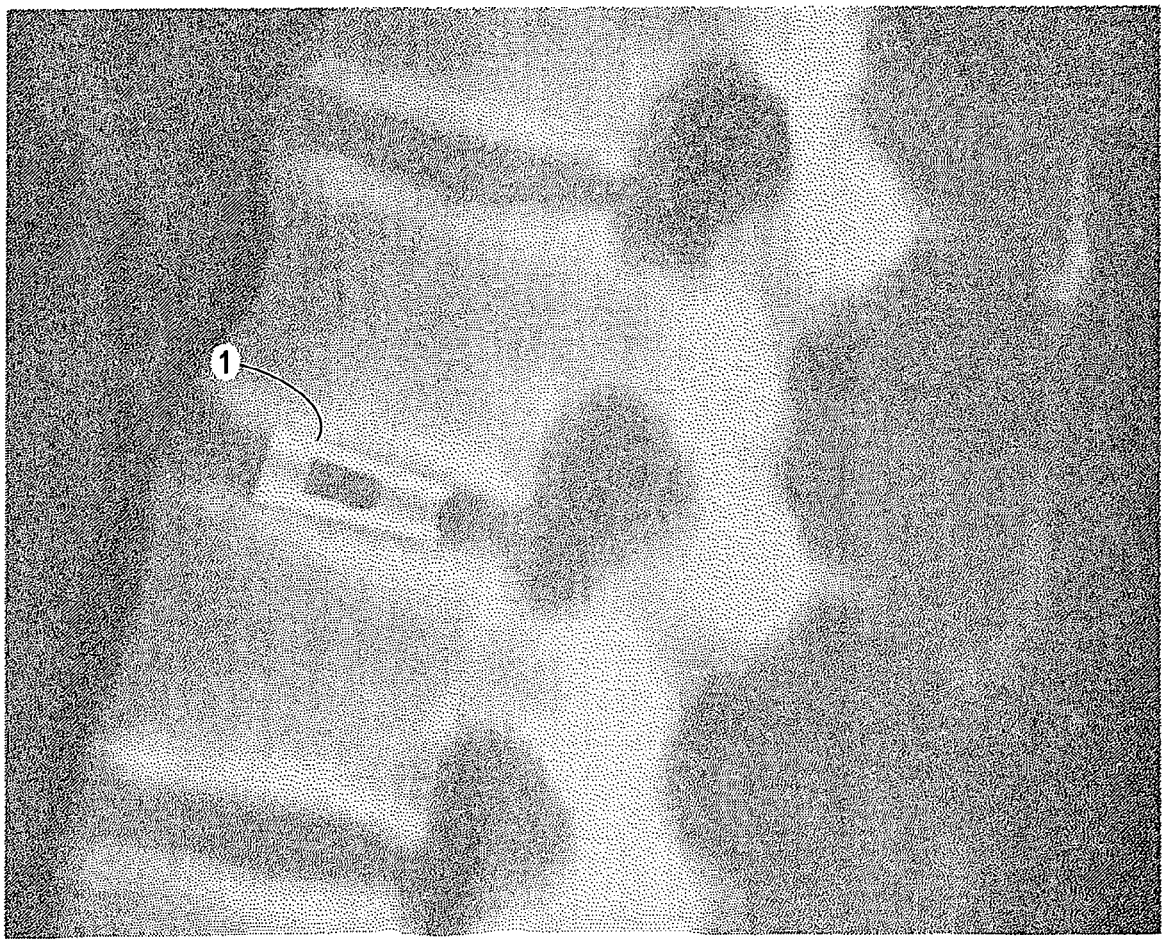

Certain embodiments of the present invention include a body having a top surface (10), a bottom surface (20), opposing lateral sides (30), and opposing anterior (40) and posterior (50) portions. The implant (1) has a sharp edge (8) where the anterior portion (40) meets the top surface (10) and where the anterior portion (40) meets the bottom surface (20). Preferred embodiments of the present interbody spinal implant are substantially hollow and have a generally oval-shaped transverse cross-sectional area with smooth and/or rounded lateral sides and rounded posterior-lateral corners. Substantially hollow, as used herein, means at least about 33% of the interior volume of the interbody spinal implant is vacant. The implant includes at least one aperture (60) that extends the entire height of the implant body. Vertical aperture (60) further defines a transverse rim (100) having greater posterior portion thickness (55) than anterior portion thickness (45). The implant may further include at least one aperture (70) that extends the entire transverse length of the implant body. As shown in FIGS. 5A-5C, these transverse apertures may provide improved visibility of the implant during surgical procedures to ensure proper implant seating and placement, and may also improve post-operative assessment of implant fusion. Still further, the substantially hollow area may be filled with cancellous autograft bone, allograft bone, demineralized bone matrix (DBM), porous synthetic bone graft substitute, bone morphogenic protein (BMP), or combinations thereof, to facilitate the formation of a solid fusion column within the patient's spine.

In at least one embodiment, the opposing lateral sides (30) and anterior portion (40) have a rim thickness of 5 mm, while the posterior portion (50) has a rim thickness of 7 mm. Thus, posterior rim thickness (55) may allow for better stress sharing between the implant and the adjacent vertebral endplates and helps to compensate for the weaker posterior endplate bone. In certain preferred embodiments transverse rim (100), having a generally large surface area, contacts the vertebral endplate. This rim may act to better distribute contact stresses upon the implant, and hence minimize the risk of subsidence while maximizing contact with the apophyseal supportive bone.

The implant further includes roughened surface topography (80) on at least a portion of its top and/or bottom surfaces for gripping adjacent bone and inhibiting migration of the implant. Roughened surface topography (80) may be obtained through a variety of techniques including, without limitation, chemical etching, shot peening, plasma etching, laser etching, or abrasive blasting, such as sand or grit blasting. In at least one embodiment, the interbody spinal implant may be comprised of titanium, or a titanium alloy, having a roughened surface topography.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may be, at least in part, dependant on the attachment and proliferation of osteoblasts, and like functioning, cells upon the implant surface. Still further, it appears that these cells attach more readily to relatively rough surfaces rather than smooth surfaces. In this manner, a surface may be bioactive due to its ability to facilitate cellular attachment and osteointegration. Without being limited by theory, it is believed that roughened surface topography (80) may better promote the osteointegration of certain preferred embodiments of the present invention. Roughened surface topography (80) may also better grip the vertebral endplate surface(s) and inhibit implant migration upon seating/placement.

In a preferred embodiment of the present invention, the roughened surface topography is obtained via the repetitive masking and chemical or electrochemical milling processes described in U.S. Pat. Nos. 5,258,098; 5,507,815; 5,922,029; and 6,193,762, each incorporated herein by reference. By way of example, an etchant mixture of nitric acid and hydrofluoric (HF) acid may be repeatedly applied to a titanium surface to produce an average etch depth of about 0.53 mm (0.021 inches). Interbody spinal implants, in accordance with preferred embodiments of the present invention, may be comprised of titanium, or a titanium alloy, having an average surface roughness of about 100 µm on its top and/or bottom surfaces. Surface roughness may be measured using a laser profilometer or other standard instrumentation.

Preferred embodiments of the present invention implant are generally shaped to reduce the risk of subsidence, and improve stability, by maximizing contact with the apophyseal rim of the vertebral endplates. Preferred embodiments may be provided in a variety of anatomical footprints having a medial-lateral width ranging from about 32 mm to about 44 mm. Interbody spinal implants, as now taught, generally do not require extensive supplemental or obstructive implantation instrumentation to maintain the prepared disc space during implantation. Thus, interbody spinal implant and associated implantation method(s), according to presently preferred aspects of the present invention, allow for larger sized implants as compared with the size-limited interbody spinal implants known in the art. This allows for greater medal-lateral width and correspondingly greater contact with the apophyseal rim.

The anterior portion (40), or trailing edge, of the implant is preferably generally greater in height than the opposing posterior portion. Accordingly, the implant may have a lordotic angle to facilitate sagittal alignment. The implant may, thus, better compensate for the generally less supportive bone found in the posterior regions of the vertebral endplate. This posterior portion of the interbody implant, preferably including the posterior-lateral corners, may also be highly radiused, thus allowing for ease of implantation into the disc space. Thus, the posterior portion may have a generally blunt nosed profile. The anterior portion (40), or trailing edge, of the implant may also preferably be configured to engage a delivery device, surgical driver, or other surgical tool.

Certain embodiments of the present invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue, and residual cartilage, may then also be removed from the vertebral endplates.

Figure 6:
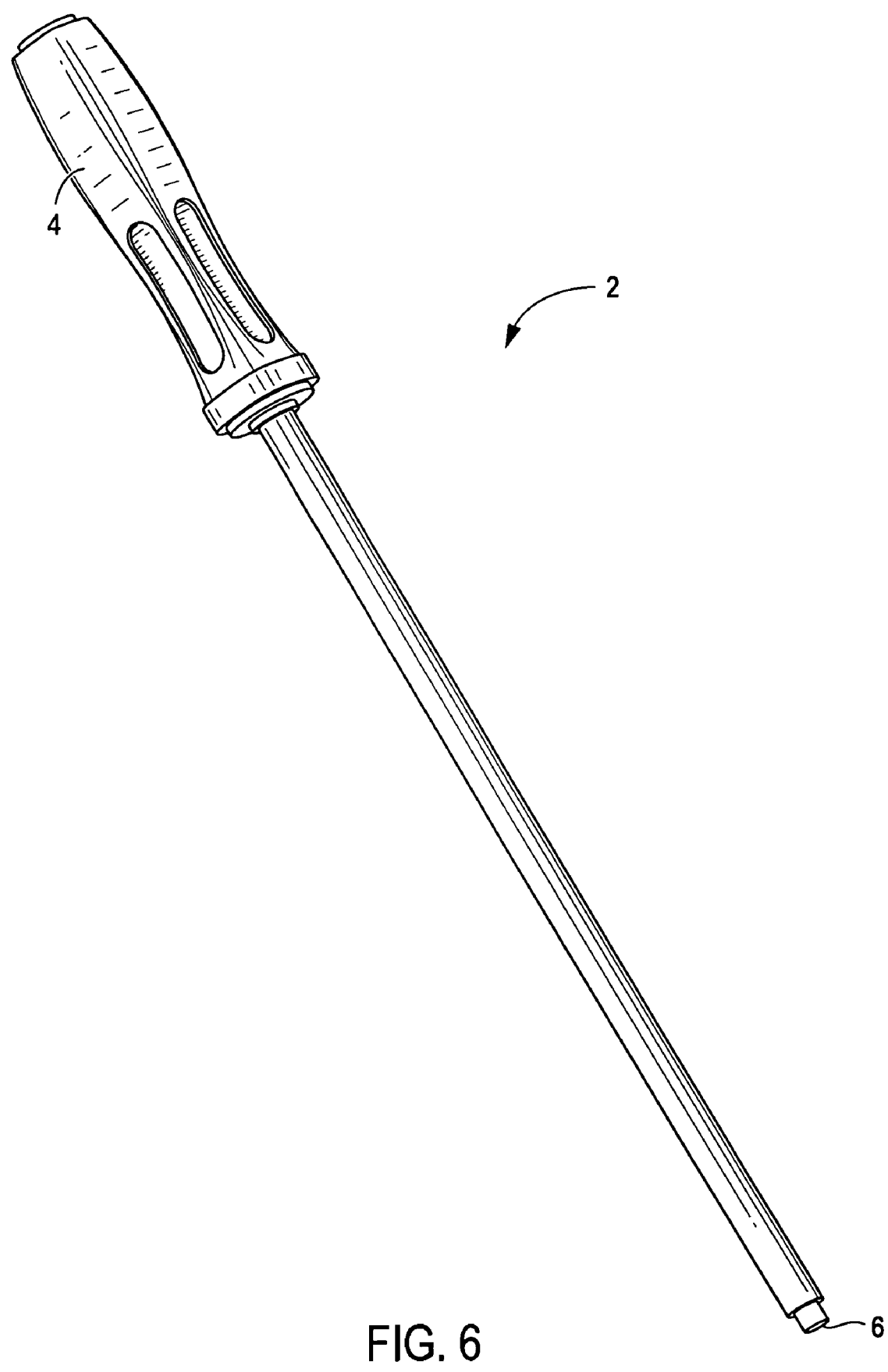
FIG. 6 shows an exemplary surgical tool (implant holder) to be used with certain preferred embodiments of the interbody spinal implant.

Vertebral distraction may be performed using trials of various-sized embodiments of the interbody spinal implant described herein. The determinatively sized interbody implant may then be inserted in the prepared disc space for final placement. The distraction procedure and final insertion may also be performed under fluoroscopic guidance. The substantially hollow area within the implant body may optionally be, at least partially, filled with bone fusion enabling materials such as, without limitation, cancellous autograft bone, allograft bone, demineralized bone matrix (DBM), porous synthetic bone graft substitute, bone morphogenic protein (BMP), or combinations thereof. Such bone fusion enabling material may be delivered to the interior of the interbody spinal implant using a delivery device mated with an opening (90) in the anterior portion of said implant. FIG. 6 shows an exemplary surgical tool, specifically an implant holder (2), to be used with certain embodiments of the interbody spinal implant (1). Typically, the implant holder (2) has a handle (4) that the caretaker can easily grasp and an end (6). In one embodiment, the anterior portion (40) has the opening (90) while the posterior portion (50) has an opening (92). Interbody spinal implants, as now taught, are generally larger than those currently known in the art, and therefore have a correspondingly larger hollow area which may deliver larger volumes of fusion enabling bone graft material. The bone graft material may be delivered such that it fills the full volume, or less than the full volume, of the implant interior and surrounding disc space appropriately.

EXAMPLE 1

Certain embodiments of the present invention are particularly suited for use during interbody spinal implant procedures currently known in the art. For example, the disc space may be accessed using a standard mini open retroperitoneal laparotomy approach. The center of the disc space is located by anterior-posterior (AP) fluoroscopy taking care to make sure the pedicles are equidistant from the spinous process. The disc space is then incised by making a window in the annulus for insertion of certain embodiments of the present spinal implant. The endplates are cleaned of all cartilage with a curette and a size-specific rasp may then be used.

Figure 7:
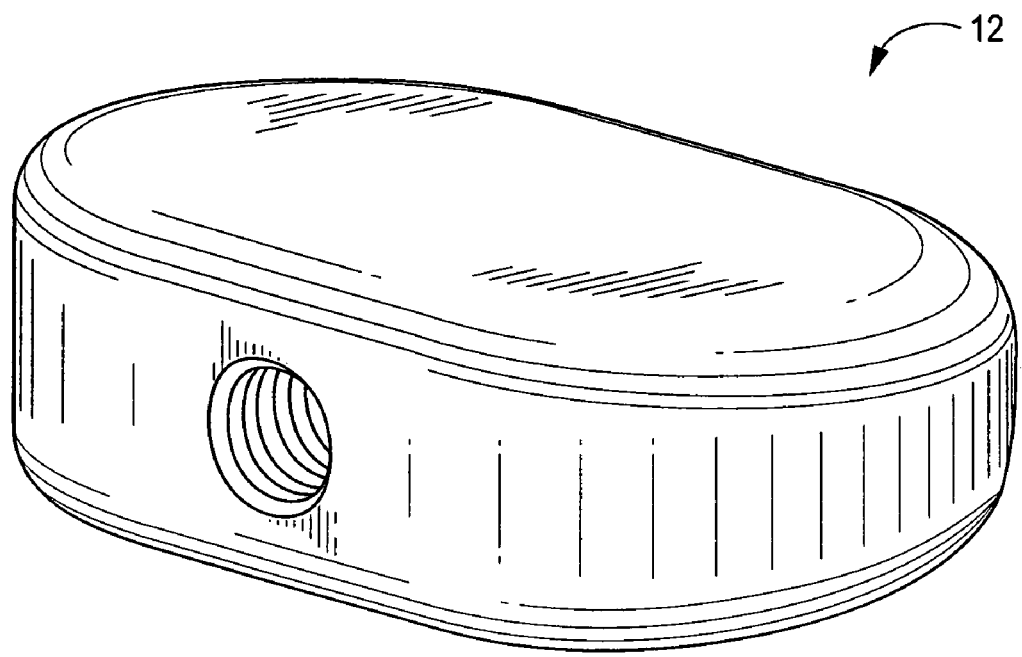
FIG. 7 shows an exemplary distractor (12) used during certain preferred methods of implantation.

A lateral c-arm fluoroscopy can be used to follow insertion of the rasp in the posterior disc space. The smallest height rasp that touches both endplates (e.g., the superior and inferior endplates) in first chosen. After the disc space is cleared of all soft tissue and cartilage, distraction is then accomplished by using implant trials or distractors or both. The implant trials, or distractors, are solid polished blocks which have a peripheral geometry identical to that of the implant. These distractor blocks may be made in various heights to match the height of the implant. An exemplary distractor block may be found in FIG. 7. The disc space is adequately distracted by sequentially expanding it with distractors of progressively increasing heights. The distractor is then left in the disc space and the centering location may be checked by placing the c-arm back into the AP position. If the location is confirmed as correct (e.g., centered), the c-arm is turned back into the lateral position. The spinal implant is filled with autologous bone graft or bone graft substitute. The distractor is removed and the spinal implant is inserted under c-arm fluoroscopy visualization.

Figure 8:
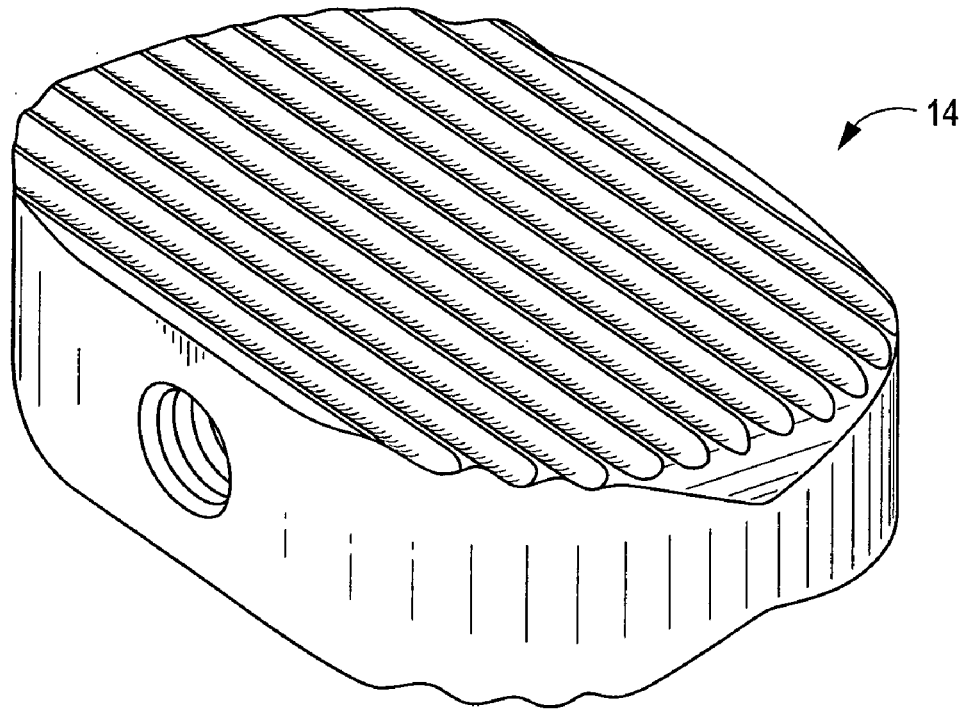
FIG. 8 shows an exemplary rasp (14) used during certain preferred methods of implantation.

Use of a size-specific rasp, as shown in FIG. 8, preferably minimizes removal of bone, thus minimizing impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load. During traditional fusion procedures, the vertebral endplate natural arch may be significantly removed due to excessive surface preparation for implant placement/seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body. Preferred embodiments of the present surgical method minimize endplate bone removal on the whole, while still allowing for some removal along the vertebral endplate far lateral edges where the subchondral bone is thickest. Still further, certain preferred embodiments of the present interbody spinal implant include smooth, rounded, and highly radiused posterior and lateral edges which may minimize extraneous bone removal for endplate preparation. Thus, interbody surgical implants and methods of using same, as now taught, are particularly useful in preserving the natural arch of the vertebral endplate and minimizing the chance of implant subsidence.

Interbody spinal implants of the present invention are durable and can be impacted between the endplates with standard instrumentation. As such, certain preferred aspects of the present invention may be used as the final distractor during implantation. In this manner, the disc space may be under-distracted, e.g., distracted to some height less than the height of the interbody spinal implant, to facilitate press-fit implantation. Further, certain preferred embodiments of the current invention having a smooth and rounded posterior portion (and lateral sides) may facilitate easier insertion into the disc space. Still further, those preferred embodiments having roughened surface topography, as now taught, may lessen the risk of excessive bone removal during distraction as compared to implants having teeth, ridges or threads currently known in the art even in view of a press-fit surgical distraction method. Nonetheless, once implanted, interbody surgical implants, as now taught, may provide secure seating and prove difficult to remove. Thus, a preferred embodiments of the present interbody spinal implant may maintain its position between the vertebral endplates due, at least in part, to resultant annular tension attributable to press-fit surgical implantation and, post-operatively, improved osteointegration at its top and/or bottom surfaces.

As previously mentioned, surgical implants and methods, as now taught, tension the vertebral annulus via distraction. These preferred embodiments and methods may also restore spinal lordosis, thus improving sagittal and coronal alignment. Implant systems currently known in the art require additional instrumentation, such as distraction plugs, to tension the annulus. However, these distraction plugs require further tertiary instrumentation to maintain the lordotic correction during actual spinal implant insertion. If tertiary instrumentation is not used, then some amount of lordotic correction may be lost upon distraction plug removal. Interbody spinal implants, according to certain preferred embodiments of the present invention, are particularly advantageous in improving spinal lordosis without the need for tertiary instrumentation, thus reducing the instrument load upon the surgeon. This reduced instrument load may further decrease the complexity, and required steps, of the implantation procedure.

Certain preferred embodiments may also reduce spondylolythesis via distraction implantation methods, as now taught. Traditional implant systems require secondary or additional instrumentation to maintain the relative position of the vertebrae. In contrast, interbody spinal implants, as now taught, may be used as the final distractor and thus maintain the relative position of the vertebrae without the need for secondary instrumentation.

Those skilled in the art will appreciate that numerous changes and modifications can be made to the many embodiments of the invention and that such changes and modifications can be made without departing from the spirit of the invention. It is therefore intended that the appended claims cover all such equivalent variations as falling within the true spirit and scope of the invention

What is claimed:

1. An interbody spinal implant generally oval-shaped in transverse cross-section and comprising:
   a top surface, a bottom surface, opposing lateral sides, and opposing anterior and posterior portions, the posterior portion defining a leading end for insertion first into a disc space and having a generally blunt nosed profile;
   blunt and radiused intersections defined along the entire lengths between the top surface and the posterior portion, the bottom surface and the posterior portion, the top surface and the lateral sides, and the bottom surface and the lateral sides, the intersections facilitating implantation; and
   a sharp edge between the top and bottom surfaces and the anterior portion to provide secure seating and resist removal;
   the spinal implant being substantially hollow and having a centrally disposed vertical aperture extending from the top surface to the bottom surface and defining a transverse rim in the top and bottom surfaces having a greater first thickness in the area of the posterior portion than a second thickness in the area of the anterior portion to improve utilization of the vertebrae.

2. The spinal implant of claim 1, wherein at least a portion of the top surface, the bottom surface, or both have a roughened surface topography.

3. The spinal implant of claim 2, wherein the roughened surface topography is chemically etched.

4. The spinal implant of claim 2, wherein the roughened surface topography is bioactive.

5. The spinal implant of claim 2, wherein the posterior portion is, and the lateral sides are, substantially smooth.

6. The spinal implant of claim 1, wherein the transverse rim in the area of the lateral sides has the second thickness and the first thickness is at least 20% greater than the second thickness.

7. The spinal implant of claim 1 further having at least one transverse aperture extending between the lateral sides.

8. The spinal implant of claim 1, wherein the anterior portion is generally greater in vertical height than the posterior portion.

9. The spinal implant of claim 1, wherein the anterior portion is substantially flat.

10. The spinal implant of claim 1, wherein the anterior portion is generally adapted to receive a delivery device.

11. The spinal implant of claim 1, wherein the posterior portion includes at least one aperture.

12. The spinal implant of claim 1 further comprising a medial-lateral width of about 32 mm to about 44 mm.

13. The spinal implant of claim 1 further comprising cancellous autograft bone, allograft bone, demineralized bone matrix (DBM), porous synthetic bone graft substitute, bone morphogenic protein (BMP), or combinations thereof.

\* \* \* \* \*